United States Patent
Nüsser et al.

(10) Patent No.: US 7,859,156 B2
(45) Date of Patent: Dec. 28, 2010

(54) HARD MAGNETIC OBJECT AND METHOD FOR ADJUSTING THE DIRECTION AND POSITION OF A MAGNETIC VECTOR

(75) Inventors: Peter Nüsser, Berlin (DE); Conrad Kauffeldt, Berlin (DE); Werner Neumann, Berlin (DE); Kurt Graichen, Berlin (DE); Andreas Arndt, Berlin (DE)

(73) Assignee: Berlin Heart GmbH, Berlin (DE)

( * ) Notice: Subject to any disclaimer, the term of this patent is extended or adjusted under 35 U.S.C. 154(b) by 251 days.

(21) Appl. No.: 11/856,427

(22) Filed: Sep. 17, 2007

(65) Prior Publication Data

US 2008/0051622 A1 Feb. 28, 2008

Related U.S. Application Data

(63) Continuation of application No. 10/399,838, filed as application No. PCT/EP02/09522 on Aug. 26, 2002, now abandoned.

(30) Foreign Application Priority Data

Aug. 24, 2001 (DE) ................. 101 42 943

(51) Int. Cl.
*H02K 7/09* (2006.01)
(52) U.S. Cl. ............... 310/90.5; 417/423.12; 335/306; 623/3.13
(58) Field of Classification Search ........... 310/90.5, 310/43, 190, 191, 156.38, 156.43; 335/212, 335/306; 417/423.12; 623/3.13
See application file for complete search history.

(56) References Cited

U.S. PATENT DOCUMENTS 2,320,632 A   6/1943   McMaster
2,536,824 A   1/1951   Sontheim
3,233,950 A   2/1966   Baermann
3,989,777 A   11/1976  Strawson et al.

(Continued)

FOREIGN PATENT DOCUMENTS

AT      1299300      12/1972

(Continued)

*Primary Examiner*—Karl I Tamai
(74) *Attorney, Agent, or Firm*—Brinks Hofer Gilson & Lione (57) ABSTRACT

The invention relates to a hard magnetic object and a method for adjusting a magnetic vector of a hard magnetic object. Therefore, the invention has the object, to provide a hard magnetic object and a method for its manufacture, which hard magnetic object has, without being influenced by an outside magnetic circuit, a desired resultant magnetic vector, which is in the frame of a predetermined tolerance range, and furthermore, that the hard magnetic object has a higher maximal energy density compared to the State of Art. According to the invention a hard magnetic object, which magnetic vector is as far as possible within the frame of a predetermined tolerance range, consists at least of one hard magnetic moulding (1) and at least one further moulded dement (11), which are combined with each other in such a way, that by means of shape, bringing together and aligning of the moulding (1) and of the moulded element (11), a predetermined direction and position of the magnetic vector of the hard magnetic object is achieved. The magnetic vector of the hard magnetic object is the resultant magnetic vector of the magnetic vectors (4; 14) of the hard magnetic moulding (1) and of the moulded elements (11).

10 Claims, 10 Drawing Sheets

U.S. PATENT DOCUMENTS

| | | | |
|---|---|---|---|
| 4,429,229 A | 1/1984 | Gluckstern | |
| 4,536,230 A | 8/1985 | Landa et al. | |
| 4,538,130 A | 8/1985 | Gluckstern et al. | |
| 4,614,930 A | 9/1986 | Hickey et al. | |
| 4,777,464 A | 10/1988 | Takabatashi et al. | |
| 4,990,879 A | 2/1991 | Aubert | |
| 5,412,365 A | 5/1995 | Abele et al. | |
| 5,894,181 A | 4/1999 | Imlach | |
| 5,928,131 A | 7/1999 | Prem | |
| 6,074,180 A | 6/2000 | Khanwilkar et al. | |
| 6,179,773 B1 | 1/2001 | Prem et al. | |
| 6,227,820 B1 * | 5/2001 | Jarvik | 417/423.12 |
| 6,250,341 B1 | 6/2001 | Helwig | |
| 6,293,901 B1 | 9/2001 | Prem | |
| 6,302,661 B1 | 10/2001 | Khanwilkar et al. | |
| 6,363,276 B1 | 3/2002 | Prem et al. | |
| 6,375,607 B1 | 4/2002 | Prem | |
| 6,394,769 B1 | 5/2002 | Bearnson et al. | |
| 6,422,990 B1 | 7/2002 | Prem | |
| 6,545,578 B2 | 4/2003 | Yoshiyama | |
| 6,581,476 B1 * | 6/2003 | Fremerey | 73/861.77 |
| 6,595,762 B2 | 7/2003 | Khanwilkar et al. | |
| 2004/0189123 A1 | 9/2004 | Nusser et al. | |
| 2008/0051622 A1 * | 2/2008 | Nusser et al. | 600/16 |

FOREIGN PATENT DOCUMENTS

| | | |
|---|---|---|
| CH | 304762 | 4/1955 |
| DE | 935626 | 5/1955 |
| DE | 946863 | 7/1956 |
| DE | 1096795 | 1/1961 |
| DE | 2106227 | 9/1971 |
| DE | 2607197 A1 | 9/1977 |
| EP | 0161832 | 11/1985 |
| FR | 1054816 | 2/1954 |
| GB | 777315 | 6/1957 |
| GB | 2347085 | 8/2000 |
| JP | 58056401 | 4/1983 |
| JP | 03-209803 | 9/1991 |
| JP | 04-042509 | 2/1992 |
| WO | WO 99/53974 | 10/1999 |

* cited by examiner

HARD MAGNETIC OBJECT AND METHOD FOR ADJUSTING THE DIRECTION AND POSITION OF A MAGNETIC VECTOR

CROSS-REFERENCE TO RELATED APPLICATIONS

This is a continuation of application Ser. No. 10/399,838 filed Sep. 24, 2003, now abandoned which was a nationalization of PCT/EP2002/09522 having an international filing date of Aug. 26, 2002.

BACKGROUND

The invention relates to a hard magnetic object and method for adjusting a magnetic vector of a hard magnetic object according to the generic parts of claims 1 and 10.

For the varying mechanical, technical and medical applications the use of hard magnetic objects is known. Inter alia, hard magnetic objects are used for measuring devices and magnetic bearings. Magnetic bearings, especially for blood pumps, implanted as heart support pumps into the body of a human being, are in contrast to common bearings free of wear and gentle to the blood.

For some applications a more specific geometric alignment of the magnetic vector of a hard magnetic object is necessary, exceeding the common north-south alignment. Especially in bearings of blood pumps, an exact alignment and correction of the direction and of the position of the magnetic vector of the hard magnetic object is very important for ensuring the bearing clearance of the magnetic bearing.

Figure 18:
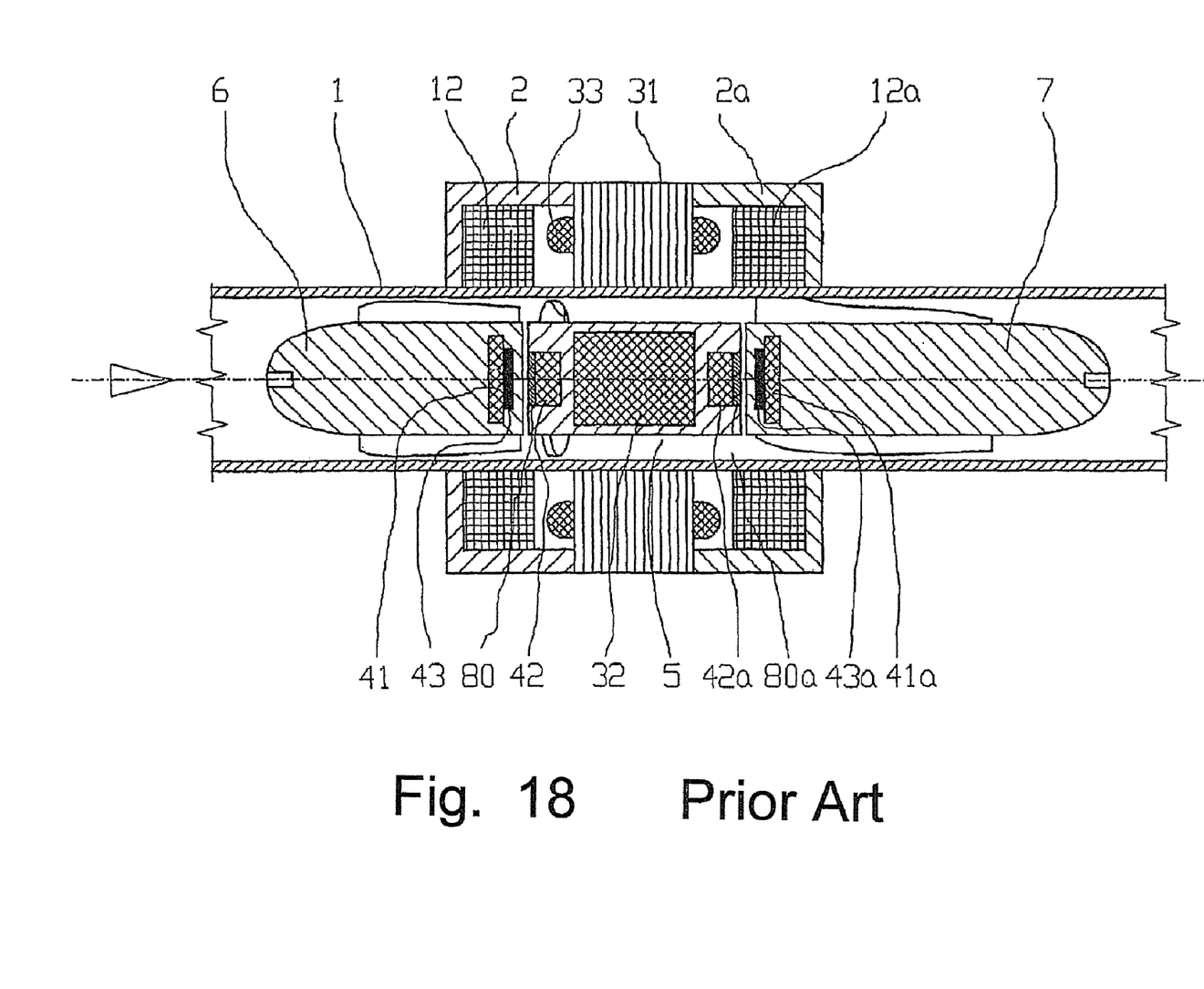
FIG. 18 an axial blood pump having magnetic bearings that can employ the hard magnetic objects.

FIG. 18 shows such an axial blood pump. The drive of the blood pump works according to the principal of an electronic commutated synchronous motor. The motor has a stator, consisting of a metal sheet packet 31, of windings 33 and iron flux return hoods 2, 2a, and a rotor 5 with a permanent magnetic core 32. The stator encloses a tubular hollow body 1, in which in axial direction a fluid, in the present case blood, is delivered. The rotor 5 is supported magnetically free of contact.

The magnetic support bearing consists of permanent magnets 42, 42a on the rotor end sides and permanent magnets 41, 41a on the end sides of the guiding devices 6 and 7. The guiding devices 6, 7 are mounted on the inner wall of the tubular hollow body 1.

To the magnetic support bearing further belong control coils 12, 12a. Sensor coils 43, 43a in the guiding devices 6, 7 and short circuit rings 80, 80a arranged opposed thereto, serve for measuring the actual rotor position.

The pairs of permanent magnets 41, 42; 41a, 42a are, respectively, polarised for attracting each other. Magnetically the pairs are arranged in series.

The control coils 12, 12a are connected electrically in series and are magnetically arranged in such a way, that a current weakens the magnetic field of the one pair of magnets and increases the magnetic field of the other pair. The magnetic flux return path is produced via the iron flux return hoods 2, 2a and the metal sheet packet 31 of the stator.

The axial position of the rotor 5 can be determined by means of the sensor coils 43, 43a. The sensor coils 43, 43a are loaded by a higher frequent voltage. By the axial movement of the rotor 5 a change of the inductively of the sensor coils 43, 43a is produced. By the arrangement of the sensor coils 43, 43a in a bridge connection a measuring signal for the axial position of the rotor 5 can be achieved.

For a bearing the bearing stiffness, the bearing clearance and the wear behaviour are generally characteristic. In a magnetic bearing the component guided in the bearing moves especially around or along an imagined magnetic axis without mechanical contact with other components of the device and independent of its mechanical geometry. During slow movements, depending on the application, a lower bearing stiffness and accuracy can be tolerated. Especially for fast rotational movements and/or large moving masses a high bearing stiffness within narrow tolerances is necessary because of the produced imbalance or the inertia of masses of the guided parts. In an axial blood pump used as an artificial heart support system for small dimensions high rotational speeds are necessary for the delivery capacity. To keep the stresses on the blood within justifiable limits in an optimised inner pump geometry, e.g. a maximal gap dimension between the rotor and the pump tube of 0.01 mm is to be maintained. Mechanical bearings (e.g. ball-bearings) would easily satisfy the mechanical requirements, but they destroy too much of the blood substance in the direct blood contact. If mechanical bearings for this application are sealingly inserted, the long term leak tightness, necessary for this application case, can not be ensured with the present State of the Art. Furthermore, at the transition between the shaft and the seal a blood damage is produced and an increased thrombosis danger exists at the boundaries of the seals. Pump rotors being free of wear and freely hovering by means of the magnetic forces, minimise these disadvantages. The bearing stiffness of the magnetic bearings of the rotor means, however, a limited bearing clearance, which cannot be undershot at a limited construction space and at hydrodynamic loadings necessary for the pump pressure. Additional bearing loadings caused by imbalances enlarge this bearing clearance. To minimise the imbalance, the magnetic bearing axis has to correspond as exactly as possible to the geometric bearing axis of the driven pump rotor. In the application case of the blood pump, for the limitation of the imbalance and for maintaining the clearance measurement, the angle deviations of the resultant magnetic vectors of the bearing magnets from the geometric rotational axis have to be below 0.3°. The common anisotropic highly coercive magnets, necessary for the capacity parameters of the magnetic bearing, have, however, measured averaged deviations of up to around 3° to the normal of the pole faces, which are oriented statistically as a bell curve distribution around the respective averaged value correspondingly to the base orientation of the starting material. Magnets traditionally made from the standard material in one piece, achieve only an immensely low yield of magnets, which have a resultant magnetic vector deviation of less than 0.3° to the pole normal.

The reason for this is, that the optimal or desired direction and size of the magnetic vector of a moulding opposes the statistically distribution of all the uncompensated spinning moments, which are responsible for the magnetic behaviour. Only in faultless single-crystals, single-range districts are present without a statistical distribution. Their application can, however, not be considered because of unsuitable material characteristics (e.g. a too low energy product) for the manufacture of magnetic bearings or other technically relevant devices. Also in materials with a distinct anisotropy a distinct statistical distribution of the uncompensated spinning moments is present with a fluctuation width, however, strongly limited. It is active macroscopically in statistical direction fluctuations of the resultant magnetic vector within a specific tolerance range.

In the most technical applications for the permanent magnets this fact plays an inferior role, as fluctuations of the magnetic vector, caused by the manufacture, around a desired zero position are tolerable.

In some applications, like, e.g. implantable blood pumps, the statistical direction fluctuations are, however, disadvantageous, as the application of permanent magnets with a magnetic vector, deviating from the desired direction, lead to an imbalance, which is too large, and therefore, to a bearing clearance, which is too large.

Therefore, it is necessary for such applications, to change or correct, respectively, the direction and position of the magnetic vector of a generally hard magnetic object in the open magnetic circuit. Such a change or correction, respectively, can be achieved in different ways.

A simple possibility is the application of an isotropic, hard magnetic material, which can be magnetised in the desired direction and strength. For such a method at the moment only hard magnetic materials are known, which cover in the maximal energy density only the lower range of the technical crest value. Materials with such a low energy density can, however, not find any application for magnetic bearings of the above described type, as the required bearing stiffnesses are not achieved.

Insofar as higher energy densities are necessary, the possibility exists, to realise the amplitude of the desired magnetic vector by means of selection of the magnetic material suitable for high energy densities, and the geometric form. The approximation to the desired direction of the magnetic vector to the geometry of the component can then be achieved when exactly knowing the position of the resulting magnetisation vector in the starting magnet by means of concerted "angle cutting". Disadvantageous are an increased work expenditure and material consumption as well as hitting accuracy of the direction of the magnetic vector to be achieved only within a distinct deviation.

Furthermore, it is known, to realise a change of the magnetic vector by means of concerted demagnetisation or magnetisation, respectively, of partial areas or the totality of a hard magnetic object. This demagnetisation or magnetisation can be achieved by means of partial fields, asymmetrical fields, a changed field gradient or other methods. Disadvantages of this method are, that in general the energy content of the magnet is not used in the full extend. This is also valid, when a change of the magnetic vector is achieved by means of using the temperature dependency of the magnetic characteristics, i.e. by means of local asymmetrical warning or cooling, respectively. Furthermore, active influencing, e.g., by means of coupling with correspondingly formed and directed coils, which are variable in the correction possibilities by means of changed drive, are known. These necessitate, however, insertion space and additional energy.

The design of other hard magnetic objects and methods for the building up of magnetic arrangements are known from GB 777 315, CH 304 762, U.S. Pat. No. 4,777,464, U.S. Pat. No. 2,320,632, DE 21 06 227 A and DE 26 07 197 A1.

In U.S. Pat. No. 2,320,632 a method for connecting permanent magnetic and soft magnetic component(s) by means of casting on of magnetic material and forming as an integrally connected magnetic component, which takes up by a slot the thermal deformation during the cooling process is described. The permanent magnetical component is, in this case, arranged between the soft magnetic pole parts. Due to this, an influence on the direction of the magnetic field of the permanent magnetic component is not possible for the above named technical applications.

In U.S. Pat. No. 777,315 and CH 304762 a magnetic yoke as a connection between permanent magnetic and soft magnetic components is described. The yoke is part of a closed magnetic circuit, e.g. in an electrical measuring device. The permanent magnetical component is arranged between soft magnetic pole pieces. Because of this, an influencing of the direction of the magnetic field of the permanent magnetic component is not possible.

In DE 2106227 A as well as DE 2607197 A1 an air gap magnetic system is described. In this case, permanent magnetic parts are imbedded in soft magnetic parts in a magnetic circuit. An influencing of the direction of the magnetic field of the permanent magnetic part is not intended and would also not be realisable, as it would be destroyed by means of the abutting soft magnetic parts.

In U.S. Pat. No. 4,777,464 also a magnetic system with an air gap, having a closed magnetic circuit is described. To a soft magnetic outer yoke two opposed permanent magnetic parts are single-sidedly coupled with the same magnetisation to the inner sides, which are combined, respectively, from two magnetic materials. On the side of these permanent magnets facing each other, the working air gap is formed with a soft magnetic pole shoe formed according to the invention. Target of the arrangement is, to achieve an as far as possible constant field distribution in the working air gap. An influencing of the direction of the magnetic field of the permanent magnetic part is not intended. The used magnets should have the same direction. Each direction change would be destroyed at the soft magnetic yoke and at the pole shoe. The amplitude of the magnetic vector is in the classical sense achieved by means of a change of the geometric relationships and dimensions of the used different sorts of magnets.

In summary it can be pointed out, that with none of the known methods the direction of the magnetic field of a hard magnetic part can be influenced. The core of the above described methods is that, by means of the closed magnetic circuit the magnetic flux, possible with the provided magnets (or coils) is coupled to a maximum into the working field of this invention (air gap in U.S. Pat. No. 2,320,632, DE 2 106 227 and DE 2 607 197 and soft magnetic test objects in U.S. Pat. No. 777,315 as well as CH 304 762), or in U.S. Pat. No. 4,777,464 it is important, that in the air gap of the magnetic field at specific values, an as constant as possible distribution of the magnetic field is achieved.

Therefore, with the known methods an alignment of the magnetic field can not be achieved. Thus, the influence at a hard magnetic object for the direction of the magnetic field is directly cancelled out by the arrangement with a closed magnetic circuit, provided in the above named methods, by means of the soft magnetic parts abutting the hard magnetic object. Therefore, each previous change or adjustment of the direction of the magnetic field is cancelled. The soft magnetic parts, not working in the saturation, concentrate in the contact face towards the hard magnetic object the magnetic flux in dependency of the difference in permeability, however, independently of the direction. The magnetic flux extends within these parts in accordance with the difference gradient of the magnetic potential. The field exits perpendicular to the upper face of the position, at which the permeability jump to the surrounding or, to the neighbouring part takes place, the soft magnetic parts. The outer path of the field lines depends then on the provided outer magnetic field conditions. In the above described methods the field lines extend mainly within the predetermined magnetic circuits. With these arrangements an-influencing of the magnetic vector is not possible.

SUMMARY

Therefore, invention is based on the object, to provide a hard magnetic object and a method for the manufacture thereof, which has, without influencing by means of an outer magnetic circuit, a desired resultant magnetic vector, which moves within the frame of a predetermined tolerance range and furthermore, that the hard magnetic object has a higher maximal energy density compared to the State of the Art.

The advantage of the invention is especially, that the adjustment or the correction, respectively, of the direction and the position of the magnetic vector of a mainly hard magnetic object can be achieved by utilisation of generally known materials in a simple way.

According to the invention a hard magnetic object, which magnetic vector is in the range of the open magnetic field largely in the frame of a predetermined tolerance range, consists of at least one hard magnetic moulding and at least of a further moulded element, which are combined with each other in such a way, that by means of shape, bringing together and alignment of the mouldings and moulded elements a predetermined direction and position of the magnetic vectors of the hard magnetic object is achieved on the predetermined side(s). The magnetic vector of the hard magnetic object is the resultant magnetic vector of the magnetic vectors of the hard magnetic moulding and the moulded elements.

The aligned hard magnetic object can also be used in closed magnetic circuits with or without an air gap. The effect of the aligned magnetic vectors is not allowed to be completely cancelled out by means of the neighbouring soft magnetic parts (e.g. pole shoes, yoke and so on), not being in the saturation state, at the aligned side in the magnetic circuit.

According to another embodiment, the moulded elements are made of materials like ferrimagnetic, ferromagnetic, antiferromagnetic, paramagnetic, superparamagnetic or diamagnetic materials.

According to yet another embodiment, the hard magnetic moulding and/or the moulded elements are formed as rotational-symmetric bodies.

One embodiment provides a non-rotational-symmetrical formation of the hard magnetic moulding and of the moulded elements.

The hard magnetic moulding and the moulded elements can be formed as compact bodies or as hollow bodies.

Advantageously, the hard magnetic moulding and the moulded elements are arranged movable relative to each other and/or fixable.

In a further embodiment of the invention, the hard magnetic moulding and the moulded elements are connected by being fixed to each other. Gluing of the parts is especially suitable for this.

In a further embodiment of the invention, the moulded element is formed as a hollow chamber in the hard magnetic moulding.

The method for the adjustment of a magnetic vector of a hard magnetic object according to the invention is characterised in that by means of connecting and aligning of hard magnetic mouldings and moulded elements an adjustment of the direction and the position of the resultant magnetic vector of the hard magnetic moulding and of the magnetic vectors of the moulded elements is carried out.

According to the method, the invention is characterised in that a predetermination of the magnetic vectors as well as of the hard magnetic moulding as well as of the moulded elements in reference to their direction and the position is carried out and following by means of further change of shape, in connection with the coupling and alignment of the moulded elements, a predetermined direction and position of the resultant magnetic vectors is achieved.

This purposeful superposition of the magnetic vectors of the mouldings according to the invention leads to a resultant magnetic vector in the frame of a predetermined tolerance range.

In a further embodiment of the method, the adjustment of the direction and the position of the resultant magnetic vector of a hard magnetic object on the predetermined sides is achieved by means of the determination and control of the resultant magnetic vectors during or after the coupling of the hard magnetic object and of the repeated purposeful changing of this arrangement correspondingly to the resulting change of the magnetic vector.

The purposeful superposition of the magnetic vector of a hard magnetic moulding with the magnetic vectors of several moulded elements according to the invention is possible with ferromagnetic, ferrimagnetic, antiferromagnetic, diamagnetic, paramagnetic or superparamagnetic materials. In this case, the moulded parts can be arranged next to each other, on top of each other, completely or partially within each other, surfacewise fully against each other, partially against each other, symmetrically or non-symmetrically to the changed axis, contorted against each other, rotationally symmetrically and inclined, and can be used inclined or straight in connection with distance effects, and can be arranged with or without change of the strength and direction by means of washers, cut inclined, abutting each other wedged-shaped or in any other way, arranged form-fittingly, glued or fixed in any other way.

The hard magnetic object according to the invention is used especially as part of a magnetic bearing.

BRIEF DESCRIPTION OF THE DRAWINGS

The invention is described in detail by means of drawings and embodiments. It shows:

FIG. 3 a hard magnetic object according to the invention consisting of a hard magnetic moulding and a moulded element, FIG. 4*a* a hard magnetic object according to the invention consisting of a hard magnetic moulding and two moulded elements, FIG. 4*b* a top view onto a hard magnetic object according to the invention, consisting of a hard magnetic moulding and two moulded elements, FIG. 5 a hard magnetic object according to the invention consisting of a hard magnetic moulding and two moulded elements, FIGS. 6 and 7 a hard magnetic object according to the invention consisting of a hard magnetic moulding, a moulded element and a soft magnetic moulded element and FIG. 8 to 17 further embodiments of hard magnetic objects.

DESCRIPTION OF PREFERRED EMBODIMENTS

Figure 1:
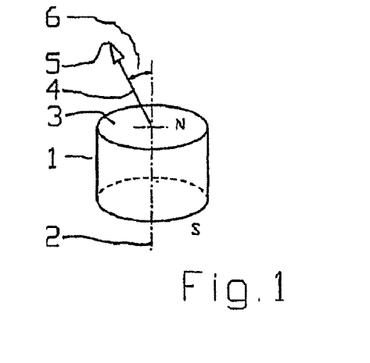
FIG. 1 a rotational formation of a hard magnetic moulding.
Figure 2:
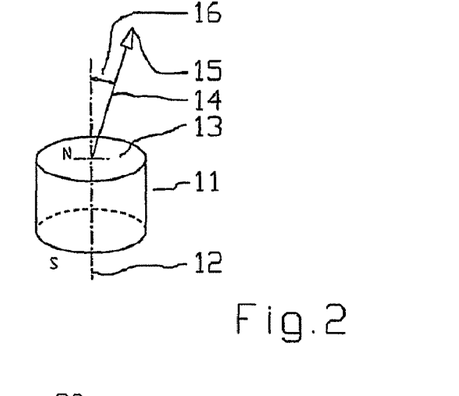
FIG. 2 a rotational-symmetrical embodiment of a further hard magnetic moulding.

FIG. 1 and FIG. 2 show a hard magnetic moulding 1 and a moulded element 11, which are formed as axially magnetised moulded elements and rotationally symmetrically. A symmetry axis 2 of the moulding 1 and a symmetry axis 12 of the moulded element 11 are arranged perpendicular on the end faces 3 and 13, formed, here exemplary as a magnetic north pole.

Figures 3, 4A, 4B, 5:
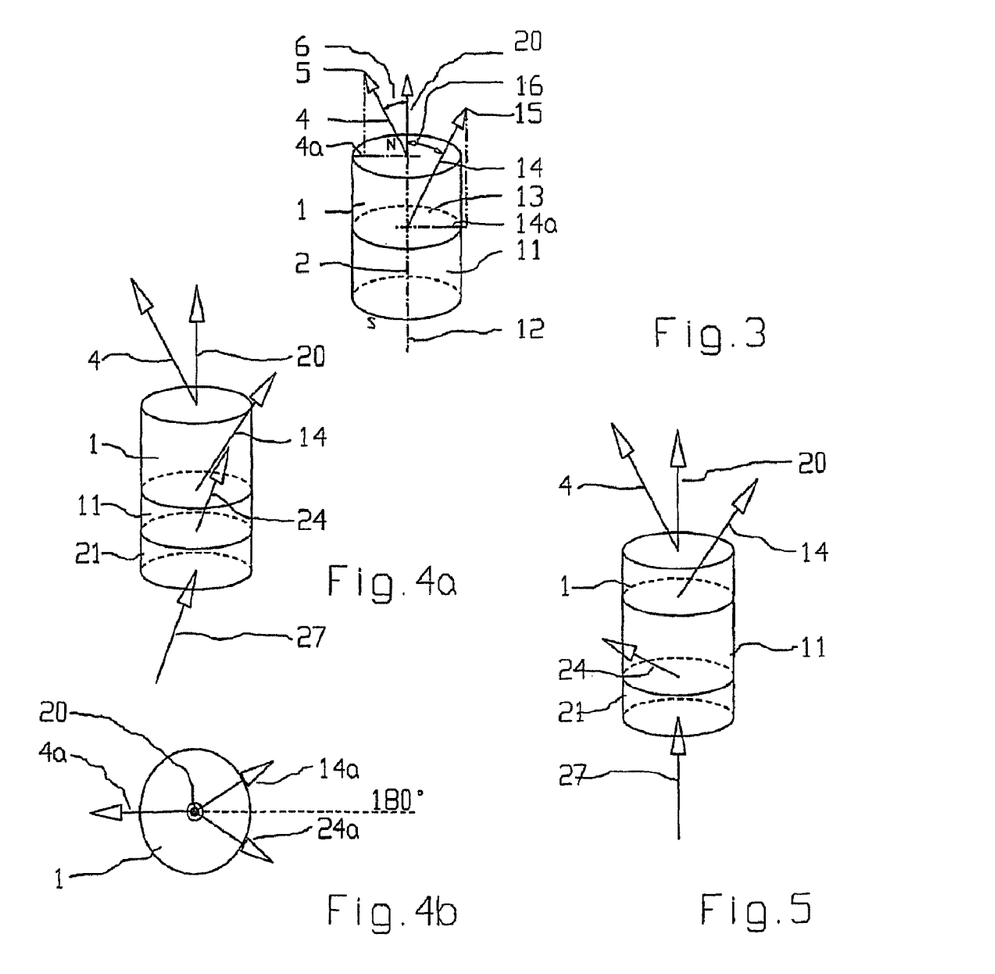

FIG. 3 shows a rotational symmetrical hard magnetic object according to the invention, consisting of a hard magnetic moulding 1 and a moulded element 11. The moulding 1 has a magnetic vector 4 having an intensity 5 (length of the vector). The moulded element 11 has a magnetic vector 14 having an intensity 15. The angles 6 and 16 symbolise the incorrect position of the magnetic vectors 4 and 14 to the desired position (here to the symmetry axis). By means of superposition of the magnetic vectors 4 and 14 a resultant magnetic vector 20 is produced, wherein the superposition of the magnetic vectors 4, 14 can be adjusted for example by means of rotating the moulding 1 or the moulded element 11, to adjust it to the predetermined tolerance range of the magnetic vector 20.

The compensation of the angles 6 and 16 in FIG. 3 is not simply achieved by means of known graphical addition. Therefore, the intensities 5 and 15 as well as the angles 6 and 16 of FIGS. 1 to 3 are only to be seen for the demonstration of the method according to the invention. In FIG. 3 only the magnetic vectors of the upper north side are shown. The resultant of the south side lies outside of the symmetry axis.

In FIG. 3 the alignment of the resultant magnetic vector 20 should fall together with the symmetry axis 2 and 12. The purposeful alignment of the magnetic vector 20 necessitates an exact measuring of the position and amplitude of the magnetic vectors of the parts. For example initially the exact position of the magnetic vector 4 of the moulding 1 is measured. The projection 4a of the magnetic vector 4 onto the north pole side is marked, for example on the end face 13 by means of a dash. The component of the magnetic vector 4 of the moulding 1, acting perpendicular to the pole normal, is to be compensated by a component of the magnetic vector 14 of the moulded element 11, active in the upper face of the moulding 1, identical to the amplitude, however, off-set by 180°. It should be noted, that it is not the measured component of the magnetic vector 14 of the moulded element 11, active perpendicular to the pole normal, but that it is the amplitude of the component of the magnetic vector 14, which after the coupling of the magnetic object is active in the upper face of the moulding 1. I.e. a value of the component, measured under measuring technical comparable conditions like moulding 1 and arranged perpendicular to the pole normal of the magnetic vector 14 of the moulded element 11, has to be larger than the component of the moulding 1 by a pairing factor dependent on the material and on the geometric dimension. The size of the amplitude of the magnetic vector directly in the normal direction of the pole is, however, not relevant for the compensation of the direction, but only for the size of the resulting amplitude of the hard magnetic object. The pairing factor has to be determined or has to be approximated by tests with following result check. The moulded element 11, having the angle value allowable for the compensation, is selected for example from a number of measured magnets being marked with the excursion direction in analogy to the moulding 1. The angle value of the moulded element 11 is only allowed to deviate in the range of an allowable fluctuation width of an angle value determined by the multiplication of the deviation angle of the moulding 1 times the dimensionless pairing factor. To align the resultant magnetic vector in direction of the rotational symmetry axis in this example, the selected moulded element 11, having a marking, which represents the projection 14a, rotated by 180° in the axis direction relative to the moulding element 1, is positioned with the magnetic north pole of the end face 13 in the centre of the magnetic south pole of the moulding 1.

FIG. 4a shows a hard magnetic object, consisting of a hard magnetic moulding 1 and the moulded elements 11, 21. In this case, the two lower moulded elements 11 and 21 produce the compensation of the angle deviation of the magnetic vector 4 of the moulding 1 from the desired position. The moulded element 21 correlates with the magnetic vector 24. The lower resultant magnetic vector 27 is not parallel to the rotational axis. The projection of the magnetic vectors 4a, 14a, 24a into the plane of the end face 3 of the hard magnetic moulding 1 is represented in FIG. 4b as a top view onto the hard magnetic moulding 1 and the moulded elements 11, 21 and explains the principal of the magnetic vector alignment. The length of the arrows corresponds to the components of the magnetic vectors 4, 14, 24 of the individual moulded parts (4a as the component of the magnetic vector 4 of the moulding 1; 14a as the component of the magnetic vector 14 of the moulded element 11; 24a as the component of the magnetic vector 24 of the moulding element 21), active in the plane 3 of the hard magnetic moulding 1 perpendicular to the rotational axis. The components 14a and 24a have to be equal and have to have at least half the amplitude of the component 4a; then by means of rotating the parts 11 and 21 against each other around the rotational axis the compensation value in reference to the deflection of the magnetic vector of the moulding 1 can be adjusted between zero and the maximal possible force and can be adapted to the compensation value. The lower resultant magnetic vector 27 is arranged in this embodiment outside of the rotational axis.

FIG. 5 shows a hard magnetic object, which consists of a hard magnetic moulding 1 and the moulded elements 11, 21 arranged on a rotational axis. In this arrangement of the vectors 4, 14, 24 the upper resultant magnetic vector 20 as well as the lower resultant magnetic vector 27 are aligned in reference to the rotational axis. The middle moulded element 11 with its magnetic vector 14 produces by means of its length and direction the compensation for the vectors 4 and 24.

Figure 6:
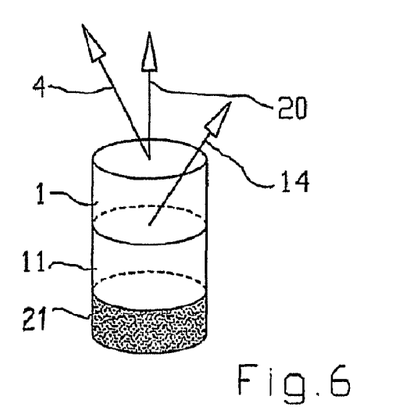

FIG. 6 shows a hard magnetic object, consisting of a moulding 1, the moulded element 11 and a soft magnetic moulded element 21, arranged on the rotational axis. In this arrangement of the vectors 4, 14, the upper resultant magnetic vector 20 is aligned in reference to the rotational axis. The middle part 11 with its magnetic vector 14 produces by means of its length and direction the compensation for the vector 4. The lower soft magnetic moulded element 21 is not arranged in saturation and neutralises the memorised angle position. The field lines exit the upper face of the soft magnetic moulded element 21 in the normal direction and follow then the outer magnetic field.

Figure 7:
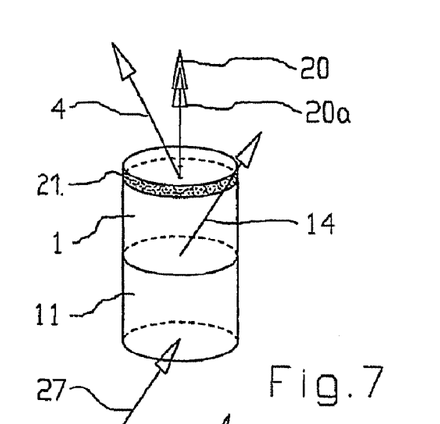

FIG. 7 shows a hard magnetic object, consisting of a soft magnetic moulded element 21 and a moulding 1 and the moulded element 11 arranged on the rotational axis. In this arrangement of the vectors 4, 14, the upper resultant magnetic vector 20 is to be aligned in reference to the rotational axis. The middle part 1 with its magnetic vector 4 produces by means of its position and direction the compensation for the vector 14 of the moulded element 11. The soft magnetic moulded element 21 compensates the small area fluctuations of the magnetic vector amplitude of the hard magnetic moulding 1 and of the moulded element 11. If the moulded element 21 is in the saturation, the direction of the magnetic vector 20 produced beforehand from the superposition of the magnetic vectors 4 and 14 (resulting vector without mouled element 21) is not neutralised. The direction of the resultant magnetic vector 20a with the mouled element 21 retains more or less the direction of the magnetic vector 20 and has, in this case, a changed amplitude.

Figure 8A:
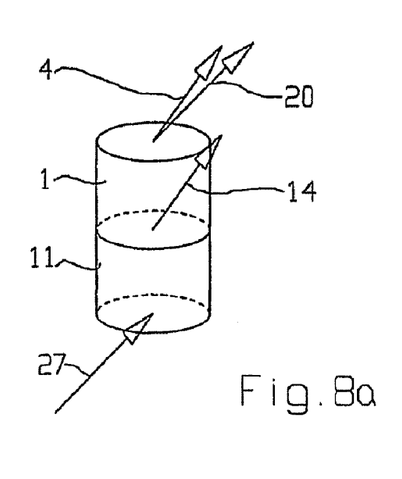
Figure 8B:
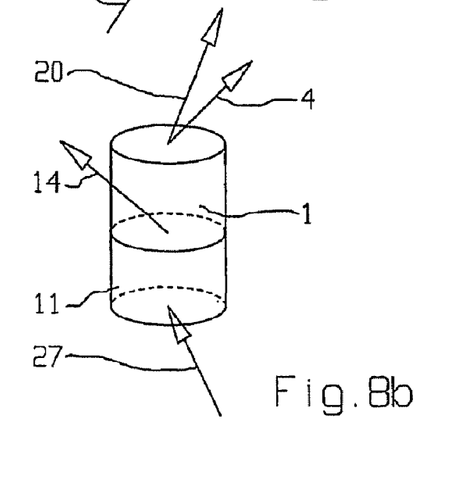

The FIGS. 8a and 8b show hard magnetic objects, consisting of a moulding 1 and the moulded element 11 arranged on the rotational axis. In this arrangement of the vectors 4, 14 the upper resultant magnetic vector 20 and the lower resultant magnetic vector 27 are aligned outside the symmetry axis.

Figure 9A:
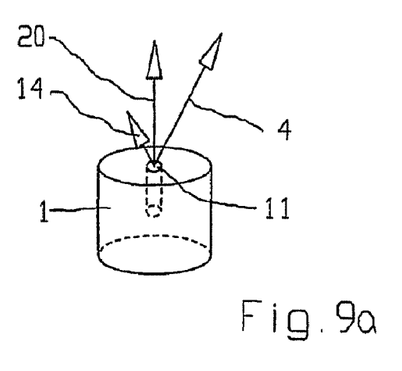
Figure 9B:
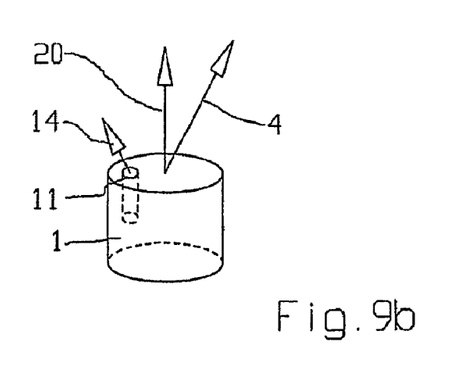
Figure 9C:
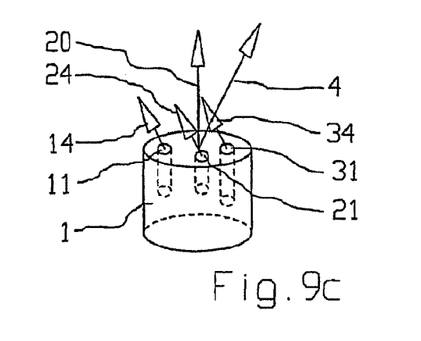
Figure 9D:
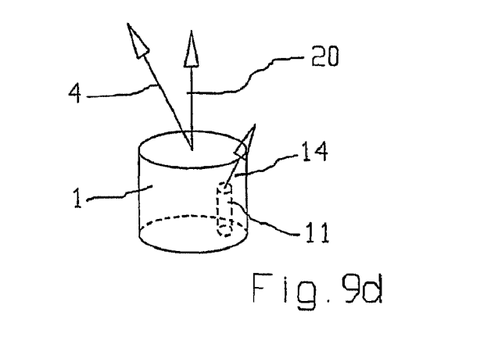
Figures 9E, 9F:
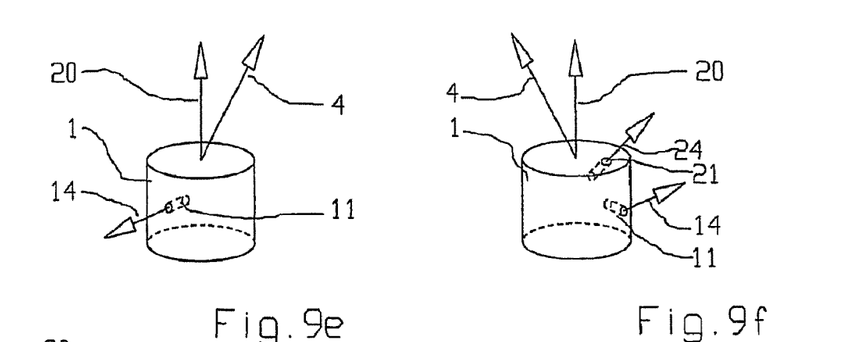

The FIGS. 9a and 9f show examples of rotational symmetrical hard magnetic objects, composed of a hard magnetic moulding 1 and one or more moulded elements 11, 21, 31, wherein the moulded elements 11, 21, 31 are formed as hollow spaces in the hard magnetic moulding 1. The alignment of the vectors is in this case, for example arrived at in such a way, that the upper resultant magnetic vector 20 coincides with the symmetry axis.

Figure 9G:
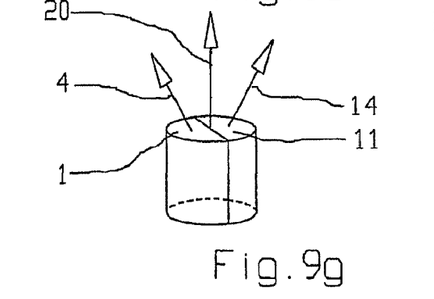
Figure 9H:
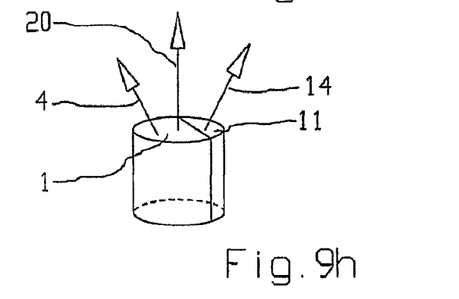

FIGS. 9g and 9h show hard magnetic objects consisting of a moulding 1 and a moulded element 11.

Figure 10A:
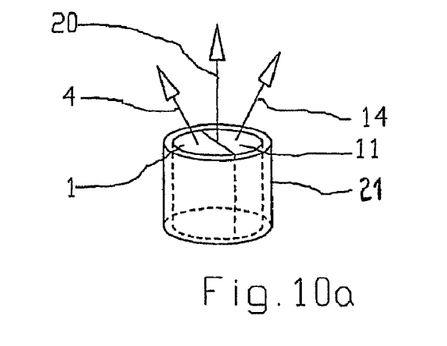
Figure 10B:
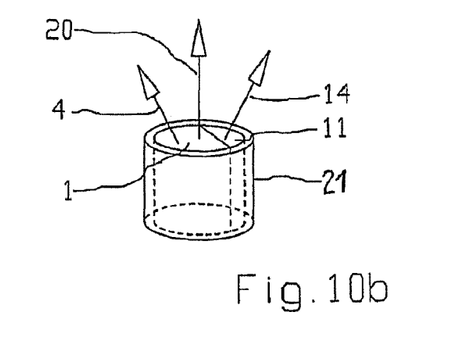
Figure 11A:
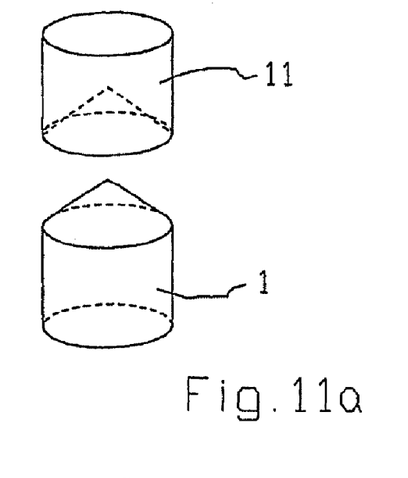
Figure 11B:
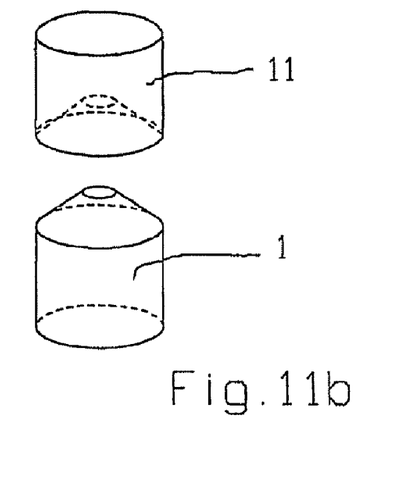
Figure 11C:
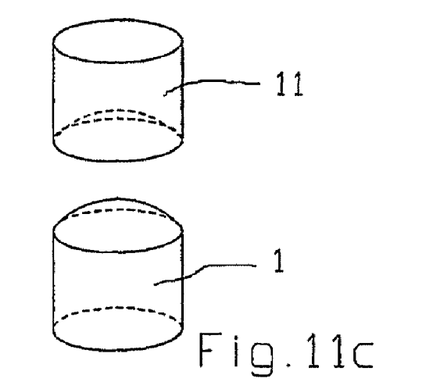
Figure 11D:
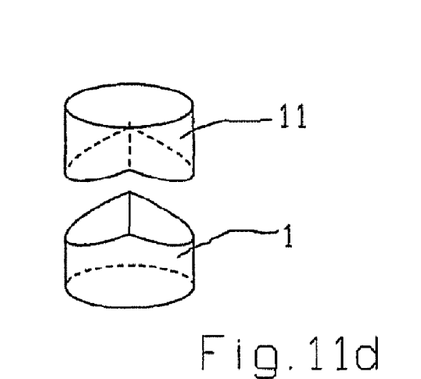
Figure 11E:
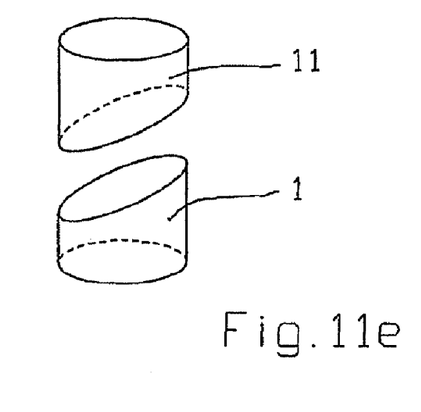
Figure 11F:
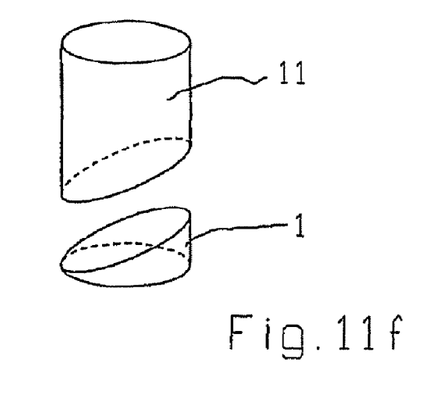

FIGS. 10a and 10b show examples of hard magnetic objects corresponding to FIGS. 9g and 9h, which are for the uptake of the repelling forces enclosed by a nonmagnetic moulded element 21 (e.g. aluminum).

FIGS. 11a to 11f show examples of rotational symmetrical hard magnetic objects, composed of respectively, one hard magnetic moulding 1 and a moulded element 11. These Figures show further examples of joining positions.

Figure 12A:
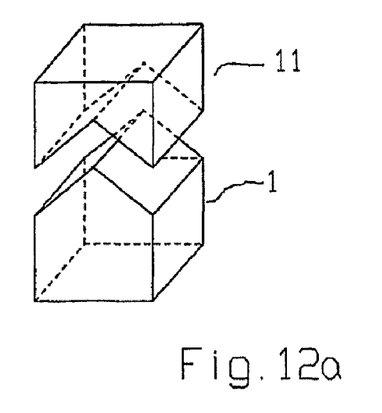
Figure 12B:
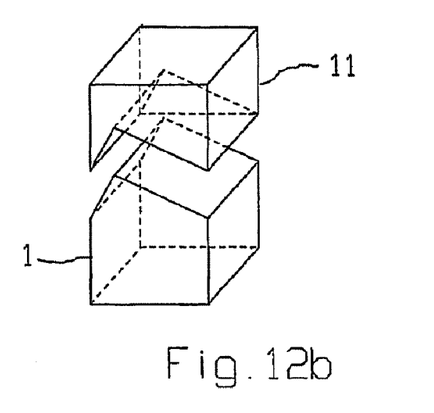
Figure 12C:
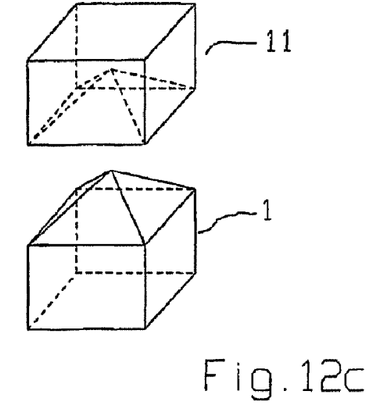
Figure 12D:
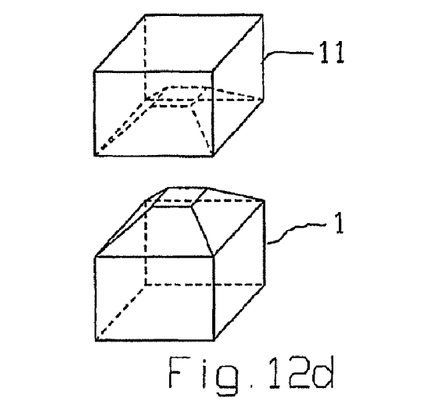
Figure 12E:
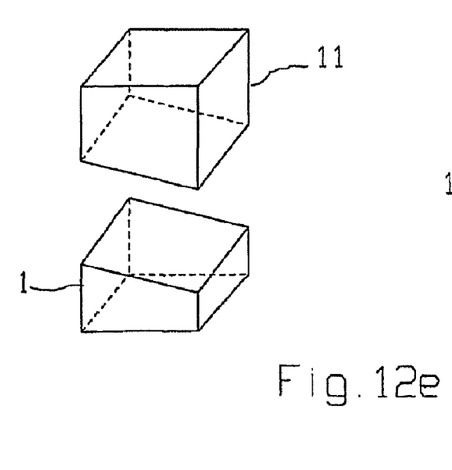
Figure 12F:
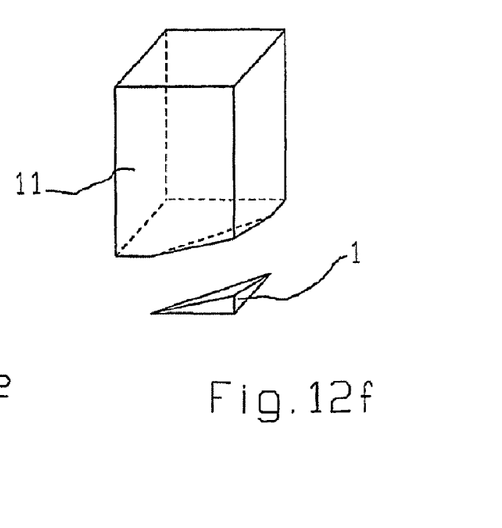
Figure 12G:
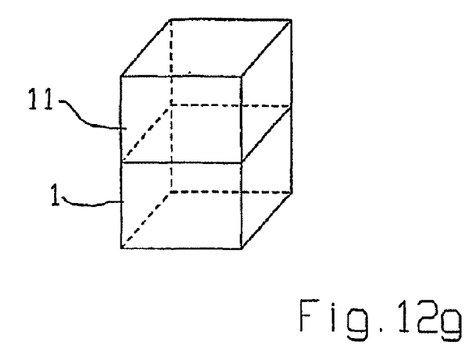
Figure 12H:
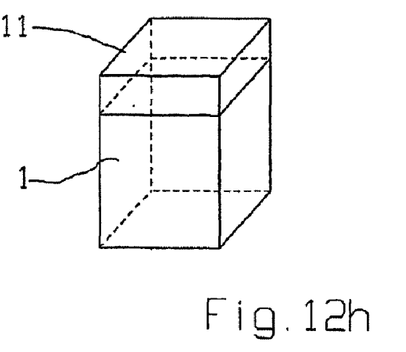
Figure 12I:
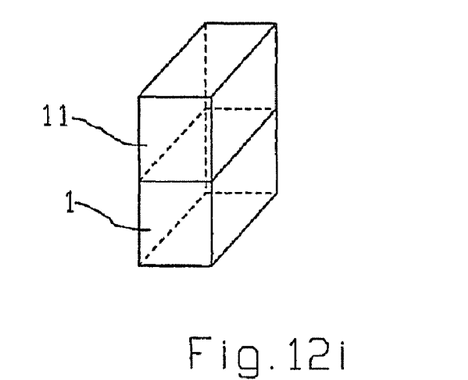
Figure 12J:
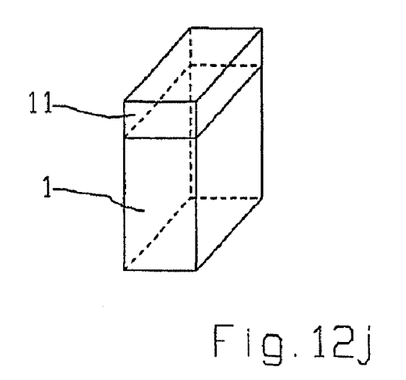
Figure 12K:
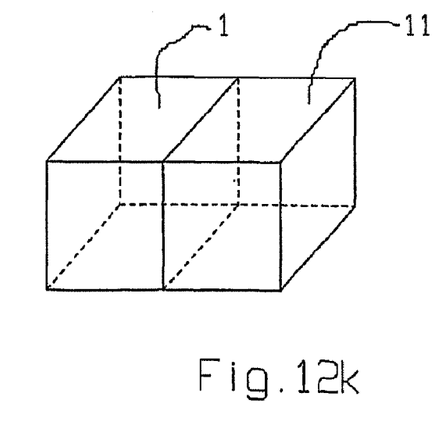
Figure 12L:
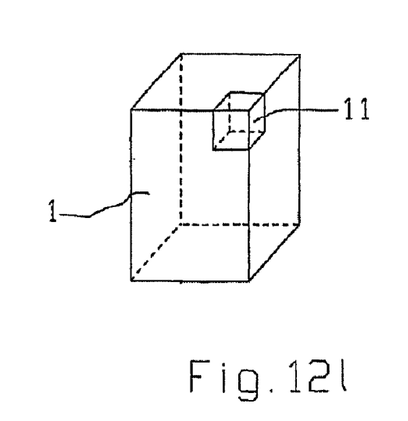
Figure 12M:
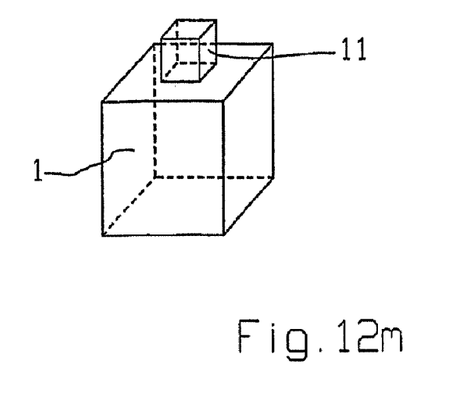
Figure 12N:
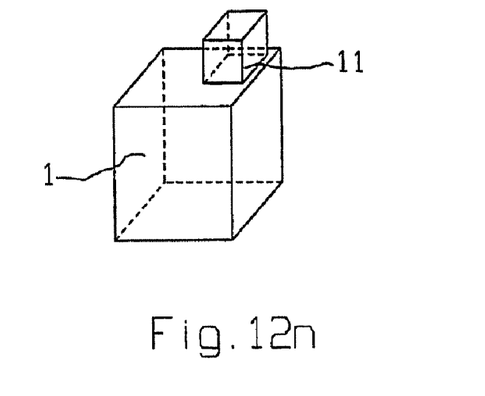
Figure 12O:
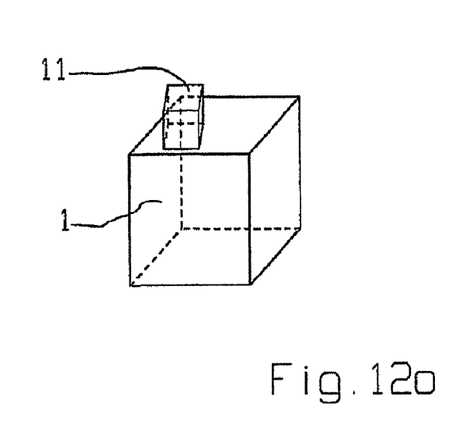
Figure 12P:
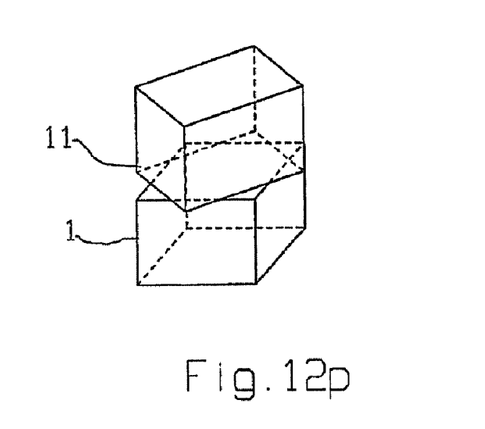
Figure 12Q:
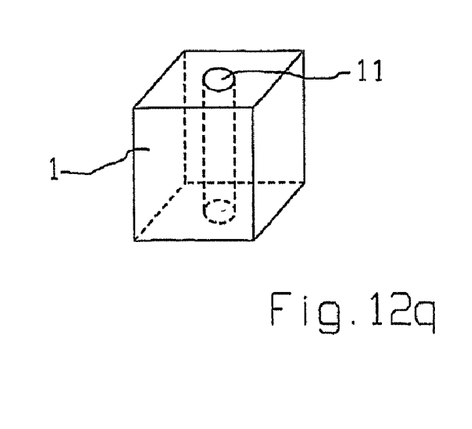
Figure 12R:
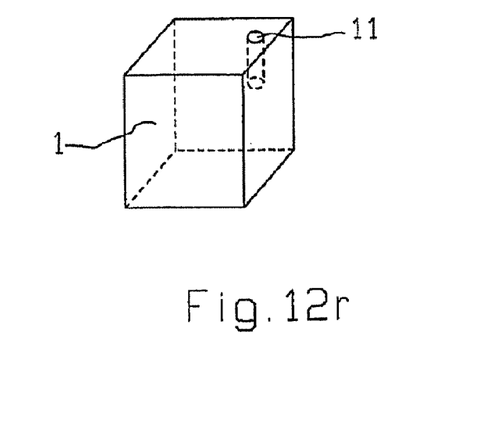
Figure 12S:
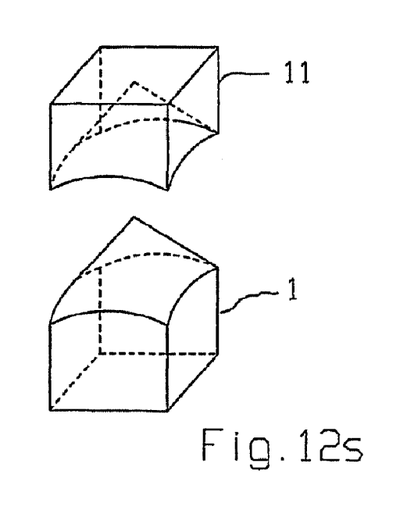

FIGS. 12a to 12s show examples of rectangular hard magnetic objects, composed of respectively a hard magnetic moulding 1 and a moulded element 11. These drawings show further examples for the composition of the components.

Figure 13A:
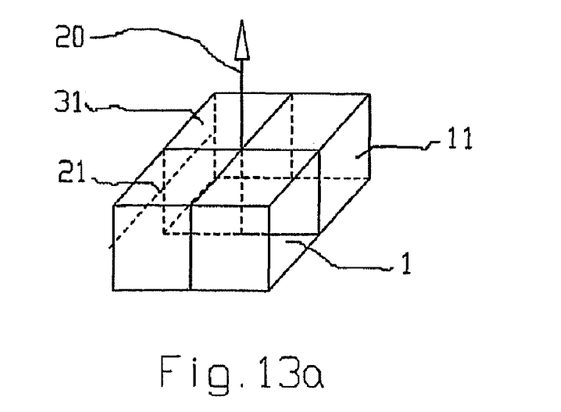
Figure 13B:
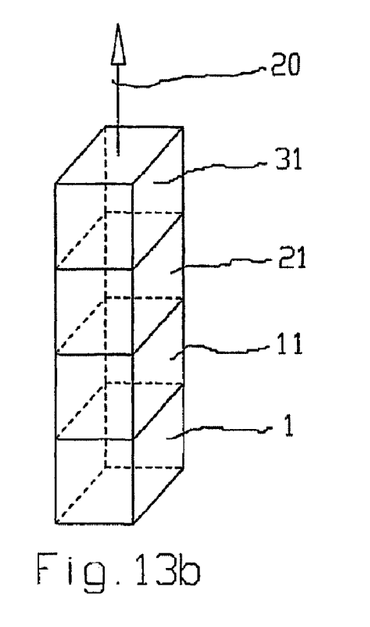

FIGS. 13a to 13b show two examples of rectangular hard magnetic objects, composed from one hard magnetic moulding and several moulded elements 11, 21, 31, to achieve a resultant magnetic vector 20 arranged in the desired position and direction.

Figure 14A:
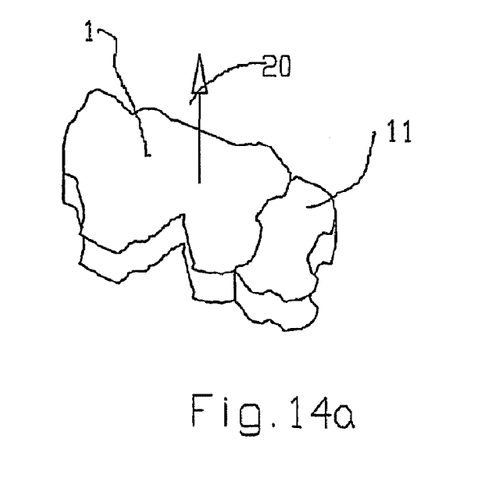
Figure 14B:
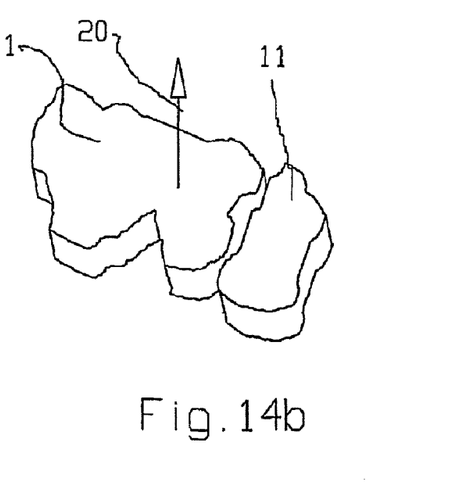

FIGS. 14a and 14b show examples of randomly formed hard magnetic objects, composed in the examples respectively from one hard magnetic moulding 1 and one moulded element 11. In the examples the resultant magnetic vector 20 is aligned in the normal direction in the magnetic centre of gravity. The hard magnetic moulding 1 and the moulded element 11 can also have (different as shown in the example) upper sides and lower sides of any form. These moulded parts can be paired in any position form-fittingly or also not fittingly with the upper face or also with a certain distance from each other (e.g. in a glued connection or casted or other), so that by means of addition of the magnetic vectors of the moulded parts the position and the direction of the resultant magnetic vector 20 are achieved.

Figure 15A:
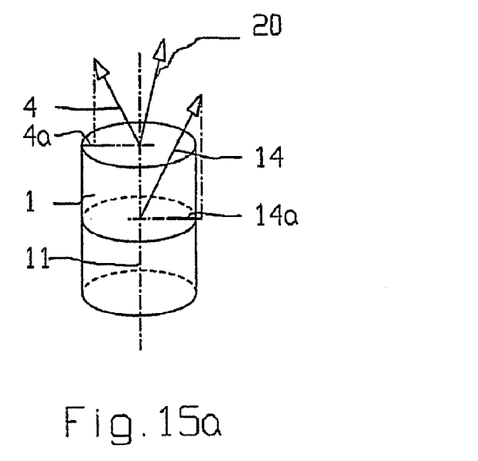
Figure 15B:
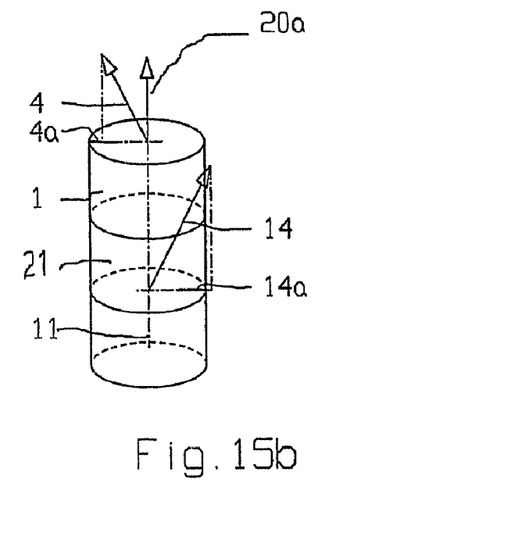
Figures 15C, 16A:
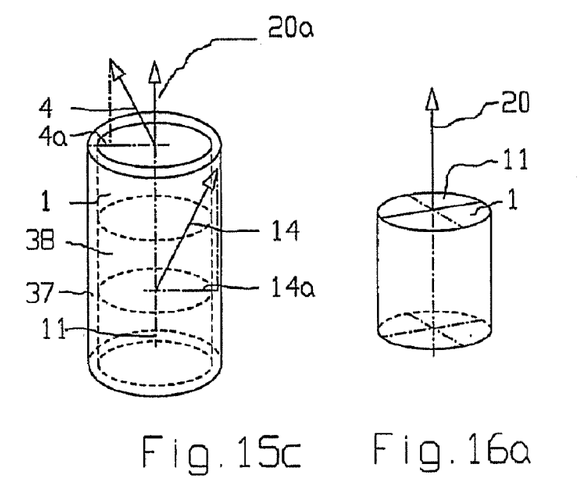

FIG. 15b shows an example of a hard magnetic object, composed from a hard magnetic moulding 1 and a moulded element 11 and a "nonmagnetic" (e.g. para- or diamagnetic) moulded element 21 and with its upper resultant magnetic vector 20 which has to coincide with the rotational axis. In FIG. 15a the fictitious starting condition is shown for explanation, in which the hard magnetic moulding 1 and the moulded element 11 are directly superposed without distance in the same alignment as in FIGS. 15b and 15c. The hard magnetic moulding 1 and the moulded element 11 produce in this fictitious starting position a resulting magnetisation vector 20 directed upwards and not coinciding with the axis of the rotational symmetry. If in this starting position the vector component of the moulded element 11, active in the upper face of the moulding 1, perpendicular to the pole normal, is larger than the vector component of the moulding 1, then the desired direction correction can be achieved by an increase of the distance. In FIGS. 15b and 15c the resultant magnetic vector 20a is corrected into the normal alignment of the magnetic vector, desired in the example, by means of the hard magnetic moulding 1 and the moulded element 11 in an alignment having the same pole, however off-set by 180°, of the vector component of the moulding 1 active perpendicular to the pole normal, and of the moulded element 11, and especially by means of a distance increase by means of a "nonmagnetic" moulded element 21 or an empty space 38 (vacuum, gaseous or liquid filling), which are fixed by means of a spacer 37.

Figure 16B:
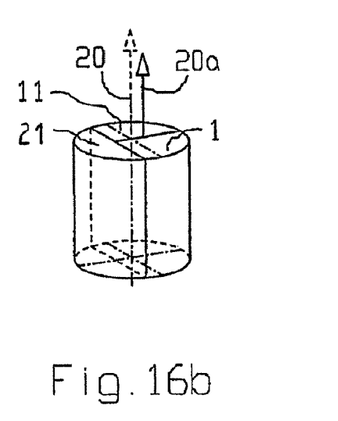

FIG. 16b shows an example of a hard magnetic object, composed of the hard magnetic moulding 1 and the moulded element 11 and a nonmagnetic (para- or diamagnetic material) moulded element 21. For explanation in FIG. 16a the fictitious starting condition for the hard magnetic object is shown corresponding to FIG. 16b. The starting moulding 1 and the starting moulded element 11 would produce in FIG. 16a in the magnetisation directed upwards, an alignment of the resulting magnetisation vector 20, coinciding with the rotational axis. In FIG. 16b the components of the moulding 1, filled by the "nonmagnetic" moulded element 21, and of the moulded element 11 are omitted. The contribution of these parts is also missing in the resultant magnetic vector 20a in correspondence with the missing parts and the position moves into the new magnetic centre of gravity outside of the rotational axis. The direction in reference to the pole plane is kept more or less. In composed moulded parts the direction may also change.

Figure 17A:
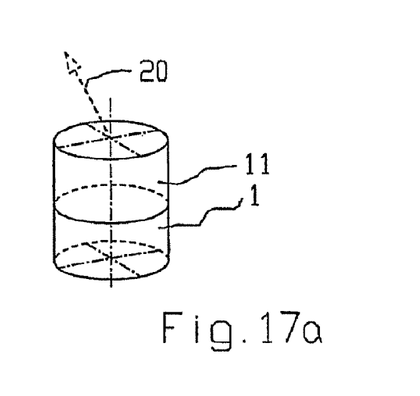
Figure 17B:
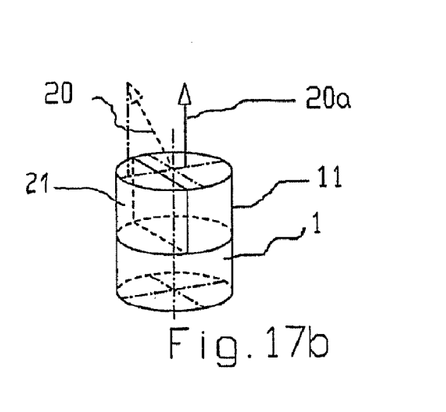

FIG. 17b shows a further example of a hard magnetic object, composed of the hard magnetic moulding 1 and the moulded element 11 and a nonmagnetic (para- or diamagnetic material) moulded element 21. For explanation reason in FIG. 17a the fictitious starting condition for the hard magnetic object is shown in correspondence to FIG. 17b. The starting moulding 1 and the starting moulded element 11 would produce in FIG. 17a in the magnetisation directed upwards, an alignment of the resultant magnetisation vector 20, which is arranged in the middle, however, does not coincide with the rotational axis. In FIG. 17b the part of the moulding 1, filled by the "nonmagnetic" moulded element 21, is omitted. The contribution of this moulded part is also missing in the resultant magnetic vector 20a of FIG. 17b. The amplitude of the resultant magnetic vector 20a decreases in correspondence with the missing part, the position moves into the new magnetic centre of gravity outside of the rotational axis and the direction changes in the example in direction of the pole normal.

The individual parts in the drawings FIG. 1 to FIG. 7 may also consist of several parts.

The invention is not limited to the here shown embodiment. Rather, it is possible, by means of combining and modifying of the named means and features to realise further variants, without leaving the scope of the invention.

REFERENCE NUMERALS LIST 1 hard magnetic moulding
2 symmetry axis
3 end face
4 upper magnetic vector
4a projection of the vector 4
5 intensity
6 angle between the magnetic vector and the symmetry axis
11 moulded element
12 symmetry axis
13 end face
14 upper magnetic vector
14a projection of the vector 14
15 intensity
16 angle between the magnetic vector and the symmetry axis
20 upper resultant magnetic vector
20a upper resultant magnetic vector
21 moulded element
24 upper magnetic vector of the moulded element 21
24a projection of the vector 24
27 lower resultant magnetic vector
31 moulded element 34 upper magnetic vector
37 spacer
38 empty space (e.g. air)

The invention claimed is:

1. An axial blood pump comprising: a rotor having an axis of rotation, magnetic bearings for suspending the rotor within the pump, at least one of the bearings including at least one hard magnetic object having a symmetry axis, the magnetic object including: at least one hard magnetic moulding having a first shape and a first magnetic vector measured to be deviating from said symmetry axis at a first angle and at least one moulded element having a second shape and selected to have a second magnetic vector deviating from said symmetry axis at a second angle, the second magnetic vector having a suitable pairing factor related to the at least one hard magnetic moulding, and wherein upon combining by aligning the at least one hard magnetic moulding and the at least one moulded element a third non-zero magnetic vector results on a front face of the magnetic object, said non-zero third magnetic vector being determined by fixedly connecting the first shape of the at least one hard magnetic moulding and the second shape of the at least one moulded element in order to point in a direction within 0.3° of the symmetry axis, the third non-zero magnetic vector of the magnetic object being substantially aligned with the axis of rotation.

2. The axial blood pump according to claim 1, wherein the at least one moulded element is chosen from the group consisting of a ferromagnetic, ferrimagnetic, antiferromagnetic, paramagnetic, superparamagnetic and a diamagnetic material.

3. The axial blood pump according to claim 1, wherein the at least one hard magnetic moulding and the at least one moulded element are both symmetrical about the symmetry axis.

4. The axial blood pump according to claim 1, wherein the at least one hard magnetic moulding and/or the at least one moulded element is a nonrotational symmetrical body.

5. The axial blood pump according to claim 1, wherein the at least one hard magnetic moulding and/or the at least one moulded element is a compact body.

6. The axial blood pump according to claim 1, wherein the at least one hard magnetic moulding and/or the at least one moulded element is a hollow body.

7. The axial blood pump according to claim 1, wherein the at least one moulded element is formed as a hollow chamber in the hard magnetic moulding.

8. A method for adjusting a magnetic vector of a magnetic bearing suspending a rotor within an axial blood pump, the blood pump rotor having an axis of rotation, the magnetic bearing including a hard magnetic object having a geometric axis of symmetry, comprising the steps of: providing a hard magnetic moulding having a first magnetic vector and having a first shape; measuring the magnitude and direction of the first magnetic vector; selecting a moulded element, having a second magnetic vector and a second shape, and having a suitable pairing factor related to the first shape of the magnetic moulding; and fixedly connecting the hard magnetic mounding and molded element to each other to form a third non-zero magnetic vector on a front face of the magnetic object by the shape of the hard magnetic moulding and the moulded element, the third non-zero vector having a desired and predetermined position and a direction deviating from the axis of symmetry by less than 0.3°, the third non-zero magnetic vector of the magnetic object being substantially aligned with the axis of rotation.

9. The method according to claim 8, further comprising the step of: initially determining the magnetic vectors of the hard magnetic moulding and the magnetic vector of the moulded element; and predetermining the resulting third vector from the initial determining step.

10. A magnetic bearing for an axial blood pump, the blood pump rotor having an axis of rotation, the magnetic bearing comprising a hard magnetic object having a symmetry axis including at least one hard magnetic moulding having a first shape and measured to have a first magnetic vector deviating from said symmetry axis at a first angle, and at least one moulded element having a second shape and selected to have a second magnetic vector deviating from said symmetry axis at a second angle, the magnetic vector being affected by a suitable pairing factor related to the at least one hard magnetic moulding, and wherein upon combining by aligning the at least one hard magnetic moulding and the at least one moulded element by engaging and fixedly connecting the first shape and the second shape, a third non-zero magnetic vector results on a front face of the magnetic object, said third non-zero magnetic vector being determined by the first shape of the at least one hard magnetic moulding and the second shape of the at least one moulded element in order to point in a direction within 0.3° of the symmetry axis, the third non-zero magnetic vector of the magnetic object being substantially aligned with the axis of rotation of the rotor.

* * * * *